(12) United States Patent
Ikeda et al.

(10) Patent No.: US 8,613,611 B2
(45) Date of Patent: Dec. 24, 2013

(54) ELECTRICALLY CONDUCTIVE POLYROTAXANE

(75) Inventors: Taichi Ikeda, Ibaraki (JP); Masayoshi Higuchi, Ibaraki (JP); Dirk G. Kurth, Ibaraki (JP)

(73) Assignee: National Institute for Materials Science, Tsukuba-shi, Ibaraki (JP)

( * ) Notice: Subject to any disclaimer, the term of this patent is extended or adjusted under 35 U.S.C. 154(b) by 39 days.

(21) Appl. No.: 13/264,474

(22) PCT Filed: Apr. 22, 2010

(86) PCT No.: PCT/JP2010/057178
§ 371 (c)(1),
(2), (4) Date: Dec. 14, 2011

(87) PCT Pub. No.: WO2010/123079
PCT Pub. Date: Oct. 28, 2010

(65) Prior Publication Data
US 2012/0083582 A1    Apr. 5, 2012

(30) Foreign Application Priority Data

Apr. 23, 2009 (JP) ................................. 2009-105010

(51) Int. Cl.
*C08G 64/00* (2006.01)
*C08G 63/02* (2006.01)

(52) U.S. Cl.
USPC .............. 425/61; 425/64; 522/111; 525/54.2; 525/55

(58) Field of Classification Search
USPC .................. 424/61, 64; 522/111; 525/54.2, 55
See application file for complete search history.

(56) References Cited

U.S. PATENT DOCUMENTS

| 5,824,470 A * | 10/1998 | Baldeschwieler et al. ... 435/6.19 |
| 2009/0149579 A1 * | 6/2009 | Ito et al. ........................... 524/96 |
| 2010/0022737 A1 | 1/2010 | Takeuchi et al. |

FOREIGN PATENT DOCUMENTS

| JP | 2004-273881 A | 9/2004 |
| JP | 2007-077030 A | 3/2007 |
| WO | 2008/069274 A1 | 6/2008 |

OTHER PUBLICATIONS

Cacialli, Franco et al., "Cyclodextrin-threaded conjugated polyrotaxanes as insulated molecular wires with reduced interstrand interactions", Nature Materials, 2002, p. 160-164, vol. 1.
Ikeda, Taichi et al., "From Thiophene [2]Rotaxane to Polythiophene Polyrotaxane", Journal of the American Chemical Society, 2009, p. 9158-9159, vol. 131.
Ikeda, Taichi et al., "Thiophene Donor—Acceptor [2] Rotaxanes", Organic Letters, 2008, p. 2215-2218, vol. 10.
Michels, Jasper et al., "Synthesis of Conjugated Polyrotaxanes", Chemistry—A European Journal, 2003, p. 6167-6176, vol. 9.
Nygaard, Sune et al., "Functionally Rigid Bistable [2]Rotaxanes", Journal of the American Chemical Society, 2007, p. 960-970, vol. 129.
Vidal, Pierre-Louis et al., "Conjugated Polyrotaxanes Incorporating Mono- or Divalent Copper Complexes", Inorganic Chemistry, 1999, p. 4203-4210, vol. 19.
Zhu, S. Sherry et al., "Conducting Polymetallorotaxanes: Metal Ion Mediated Enhancements in Conductivity and Charge Localization", Journal of the American Chemical Society, 1997, p. 12568-12577, vol. 119.
International Search Report of PCT/JP2010/057178, mailing date Jul. 13, 2010.
Supplementary European Search Report dated Jan. 25, 2012, issued in corresponding European Patent Application No. 10767136.4.
Ikeda et al.; "βSubstituted Terthiophene [2] Roxtaxanes"; Chemistry—A European Journal, vol. 15, No. 19, Mar. 23, 2009 (Feb. 23, 2009), pp. 4906-4913, XP550166611.(cited in Supplementary European Search Report dated Jan. 25, 2012).

\* cited by examiner

*Primary Examiner* — Terressa Boykin
(74) *Attorney, Agent, or Firm* — Westerman, Hattori, Daniels & Adrian, LLP

(57) ABSTRACT

The conductive polyrotaxane of the present invention contains an electron-accepting cyclic molecule in each of its repeating unit. Since the electron-accepting cyclic molecule remains stable because of molecular interaction with a π-conjugated oligomer molecule, the electron-accepting cyclic molecule is not dissociated during rotaxane polymerization reaction, and thus a conductive polyrotaxane of stable quality can be obtained.

7 Claims, 8 Drawing Sheets

ELECTRICALLY CONDUCTIVE POLYROTAXANE

TECHNICAL FIELD

The present invention relates to an electrically conductive polyrotaxane synthesized by polymerization of rotaxanes.

BACKGROUND ART

A rotaxane has a molecular structure consisting of a cyclic molecule, π-conjugated oligomer threaded through the cyclic molecule, and side chains introduced to both ends of the π-conjugated oligomer, wherein the cyclic molecule cannot be pulled out of the π-conjugated oligomer because of the existence of the side chains. A polyrotaxane, which is synthesized by oxidation polymerization of rotaxanes, has characteristics not shared by conventional polymers, and studies have been conducted on polyrotaxanes.

As disclosed in non-patent literatures 1 and 2 and patent literature 1, a conductive polyrotaxane is directly synthesized from an inclusion complex. However, if polymerization reaction should occur the moment the inclusion complex dissociates, repeating units without a cyclic molecule are synthesized within a conductive polymer.

Non-patent literatures 3 and 4 disclose a synthesis method using transition metal ions to form an inclusion complex consisting of a cyclic molecule and a conductive polymer. With this method, however, since a ligand site interacting with transition metal ions must be integrated into the main chain of the conductive polymer, π-conjugation of the conductive polymer is disconnected at the ligand site, which results in decrease in conductivity.

With the formation of an inclusion complex of an electron-accepting cyclic molecule and an electron-releasing oligomer molecule, charge transfer interaction and π-π stacking interaction play an important role to stabilize the inclusion complex. When the oligomer molecule is subjected to oxidation polymerization to form a conductive molecule, the oligomer molecule turns into a radical cation, thus losing electron-releasing property and being made to carry positive charge. Consequently reaction force against the electron-accepting cyclic molecule is generated, which causes the inclusion complex to dissociate. In other words, with the conventional method for obtaining a polyrotaxane based on polymerization of inclusion complexes, repeating units lacking a cyclic molecule is synthesized within the conductive molecule.

Since the equilibrium constant for formation and dissociation of an inclusion complex changes due to a slight difference in conditions such as temperature, solvent concentrations, and the composition of the solution, it is difficult to maintain the quality of conductive polyrotaxanes at a uniform level.

CITATION LIST

Patent Literature

[Patent Literature 1] JP 2004-273881 A

Non-Patent Literature

[Non-Patent Literature 1] Nature Materials. vol. 1(3), 160-164, Oct. 20, 2002 (online); Franco Cacialli, Joanne S. Wilson, Jasper J. Michels, Clement Daniel, Carlos Silva, Richard H. Friend, Nikolai Severin, Paolo Samori, Jurgen P. Rabe, Michael J. O'Connell, Peter N. Taylor, Harry L. Anderson.

[Non-Patent Literature 2] Chemistry—A European Journal. vol. 9(24), 6167-6176, Dec. 15, 2003; Jasper J. Michels, Michael J. O. Connell, Peter N. Taylor, Joanne S. Wilson, Franco Cacialli, Harry L. Anderson.

[Non-Patent Literature 3] Inorganic Chemistry. vol. 38(19), 4203-4210, Aug. 27, 1999; Pierre-Louis Vidal, Bernadette Divisia-Blohorn, Grard Bidan, Jean-Marc Kern, Jean-Pierre Sauvage, Jean-Louis Hazemann.

[Non-Patent Literature 4] Journal of the American Chemical Society. vol. 119(5), 12568-12577, Dec. 24, 1997; S. Sherry Zhu, Timothy M. Swager.

SUMMARY OF THE INVENTION

Technical Problem

In view of such circumstances, the present invention intends to provide a polyrotaxane having conductivity (hereinafter referred to as conductive polyrotaxane), in which a cyclic molecule is not dissociated.

Solution to Problem

The conductive polyrotaxane of the present invention is a rotaxane polymer having a π-conjugated oligomer and an electron-accepting cyclic molecule, wherein the electron-accepting cyclic molecule is contained in each repeating unit.

The conductive polyrotaxane of the present invention is also characterized in that the electron-accepting cyclic molecule has inter-molecular reaction with the π-conjugated oligomer.

The method of synthesizing a conductive polyrotaxane of the present invention is characterized in that reacting a π-conjugated oligomer, cyclic molecule precursor, and cyclizing agent in a low-polarity organic solvent to obtain a rotaxane, and subjecting the rotaxane to oxidation polymerization.

Advantageous Effect of the Invention

The conductive polyrotaxane of the present invention does not vary widely in quality such as conductivity, and can provide polymer products having stable conductivity.

DESCRIPTION OF EMBODIMENTS

The inventors pursued research on synthesis of a polyrotaxane, and succeeded in completing the present invention based on the knowledge that in a rotaxane synthesized by a π-conjugated oligomer and an electron-accepting cyclic molecule, the electron-accepting cyclic molecule is prevented from being sterically dissociated from the π-conjugated oligomer because of the side chains of the π-conjugated oligomer.

Figure 1:
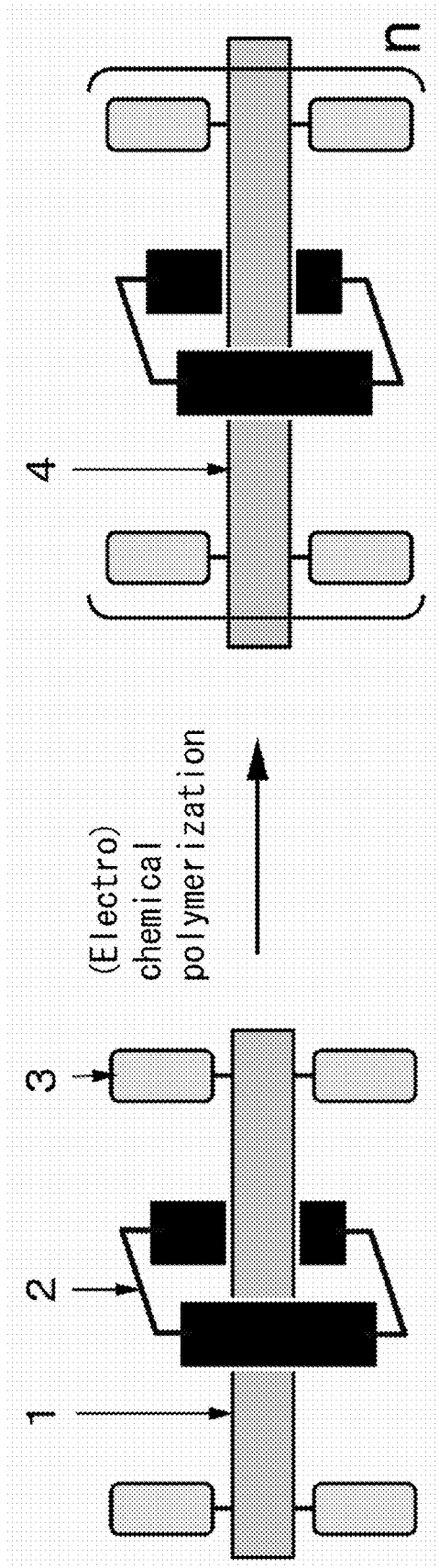
FIG. 1 is a schematic diagram showing the concept of the present invention.

FIG. 1 illustrates the concept of the present invention. Sign character 1 in FIG. 1 represents a π-conjugated oligomer, sign character 2 represents a cyclic molecule including electron-accepting part, and sign character 3 represents side chains.

Namely, the rotaxane has a basic structure having the π-conjugated oligomer 1 and the electron-accepting cyclic molecule 2, where the electron-accepting cyclic molecule 2 is prevented from being dissociated from the π-conjugated oligomer 1 because of the side chains 3 introduced into the π-conjugated oligomer 1.

In the example, a chemical compound represented by chemical formula 1 is shown as the rotaxane, and chemical formula 2 represents a cyclic molecule containing two 4,4'-bipyridinium salt regions as the electron-accepting cyclic molecule of the rotaxane. Intermolecular interaction takes place between the electron-accepting 4,4'-bipyridinium salt and the electron-releasing thiophene oligomer, and the electron-accepting cyclic molecule remains in stable state without being dissociated by oxidative condensation reaction of the rotaxane.

Chemical formula 1

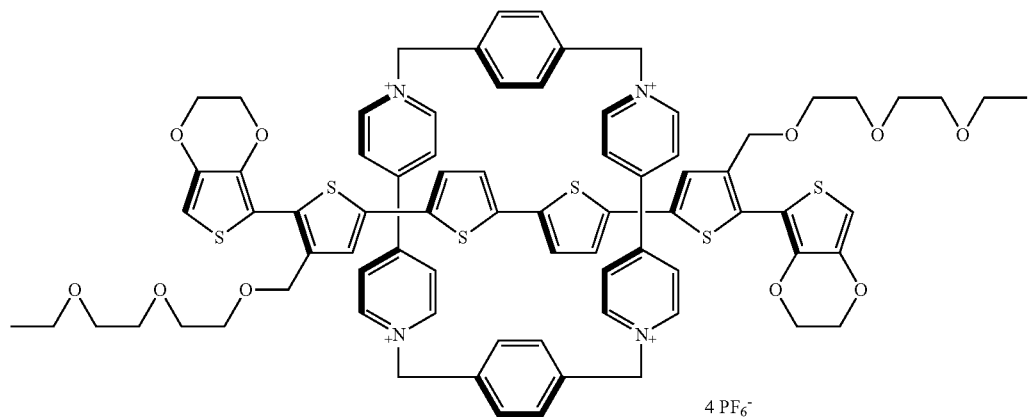

Chemical formula 2

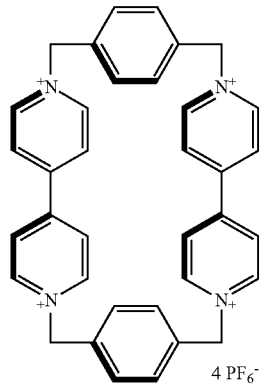

This description shows specific compound of the π-conjugated oligomer, citing an example of a thiophene hexamer derivative. However, a large number of π-conjugated oligomers that can be subjected to oxidation polymerization are known. π-conjugated oligomers that turn to conductive molecules as a result of synthesis by oxidation polymerization, such as derivatives including heterocyclic π-conjugated oligomer represented by chemical formula 4, oligophenylene represented by chemical formula 5, oligofluorene represented by chemical formula 6, oligo-aniline represented by chemical formula 7, and oligophenylene sulfide represented by chemical formula 8, derivatives partially containing the above derivatives, and mixed derivatives may be used. Since these oligomers have electron-releasing property similar to thiophene derivative, it is well imagined that synthesis of rotaxanes and that of polyrotaxanes based on oxidation polymerization are possible. Although the thiophene hexamer derivative is used in the example, it is well imagined that longer or shorter oligomers can also produce similar results.

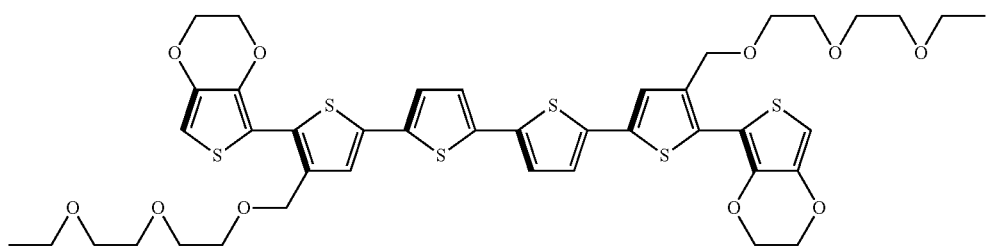

Chemical formula 3

Chemical formula 4

X = NH, O Se, Te

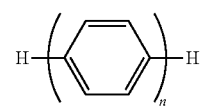

Chemical formula 5

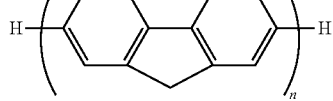

Chemical formula 6

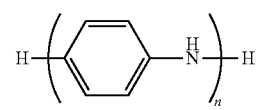

Chemical formula 7

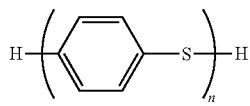

Chemical formula 8

The side chains of the π-conjugated oligomer prevent the cyclic molecule from being dissociated from the π-conjugated oligomer. Side chains of any length or chemical structure can be used, provided that they are larger than the internal diameter of the cyclic molecule (5 angstrom×11 angstrom). For example, alkyl group, ethylene glycol group having a repeating unit of 1 or higher, ethylene glycol group having a methyl group at the end and a repeating unit of 1 or higher, ethylene glycol group having an ethyl group at the end and a repeating unit of 1 or higher, ethylene glycol group having propyl group or isopropyl group at the end and a repeating unit of 1 or higher, and ethylene glycol group having a butyl group or tertiary butyl group at the end and repeating unit of 1 or higher can be used.

A rotaxane is synthesized by reacting π-conjugated oligomer, cyclic molecule precursor, and cyclizing agent to react with each other in a polar organic solvent.

In the example, as the cyclic molecule precursor, a molecule containing two 4,4'-bipyridinium salt regions can be used. In this specification, 1,1'-[1,4-phenylenebis (methylene)]bis-4,4'-bipyridinium bis (hexafluorophosphate) is used.

As the cyclizing agent, α,α'-dihalogen-p-xylene can be used. Specifically, α,α'-dibromo-p-xylene is used.

Any conductive work electrodes can be used without limitation to synthesize a polyrotaxane. Any work electrodes capable of applying a voltage sufficient to oxidize the rotaxane can be used. It has been confirmed that a film is formed with the voltage of +1.0 V (to a reference saturated calomel electrode [SCE]) or higher. Any rotaxane solution concentrations sufficient to cause polymerization can be adopted, and the concentration of $5.0 \times 10^{-5}$ M (mol) or higher was confirmed to form a film. It is well considerable that even if these conditions would be changed, similar results would be obtained.

Any oxidizing agents having oxidizing power sufficient to oxidize the π-conjugated oligomer of the rotaxane can be used to synthesize a polyrotaxane by chemical oxidation. For example, $SbCl_5$, $SbF_5$, $NOSbF_6$, $O_2SbF_6$, $O_2AsF_6$, $NOAsF_6$, $NOBF_4$, $NOClO_4$, $NOPF_6$, $FeCl_3$, $FeBr_3$, $FeI_3$, $Fe(ClO_4)_3$, $Fe(BF_4)_3$, $Fe(PF_6)_3$, $FePO_4$, $Fe(CH_3C_6H_4SO_3)_3$, $Fe(CF_3SO_3)_3$, $MoCl_5$, $RuCl_3$, $CuCl_2$, etc. can be used. It is well considerable that even if the type of oxidizing agent should be changed, similar results would be obtained.

As shown in FIG. 1, if rotaxanes are subjected to chemical or electrochemical oxidation polymerization, the rotaxane 1 turns to a conductive polymer 4, and thus a polyrotaxane is obtained.

The present invention will hereinafter be described in detail by referring to examples.

Example 1

<Synthesis of a Rotaxane>

Figure 2:
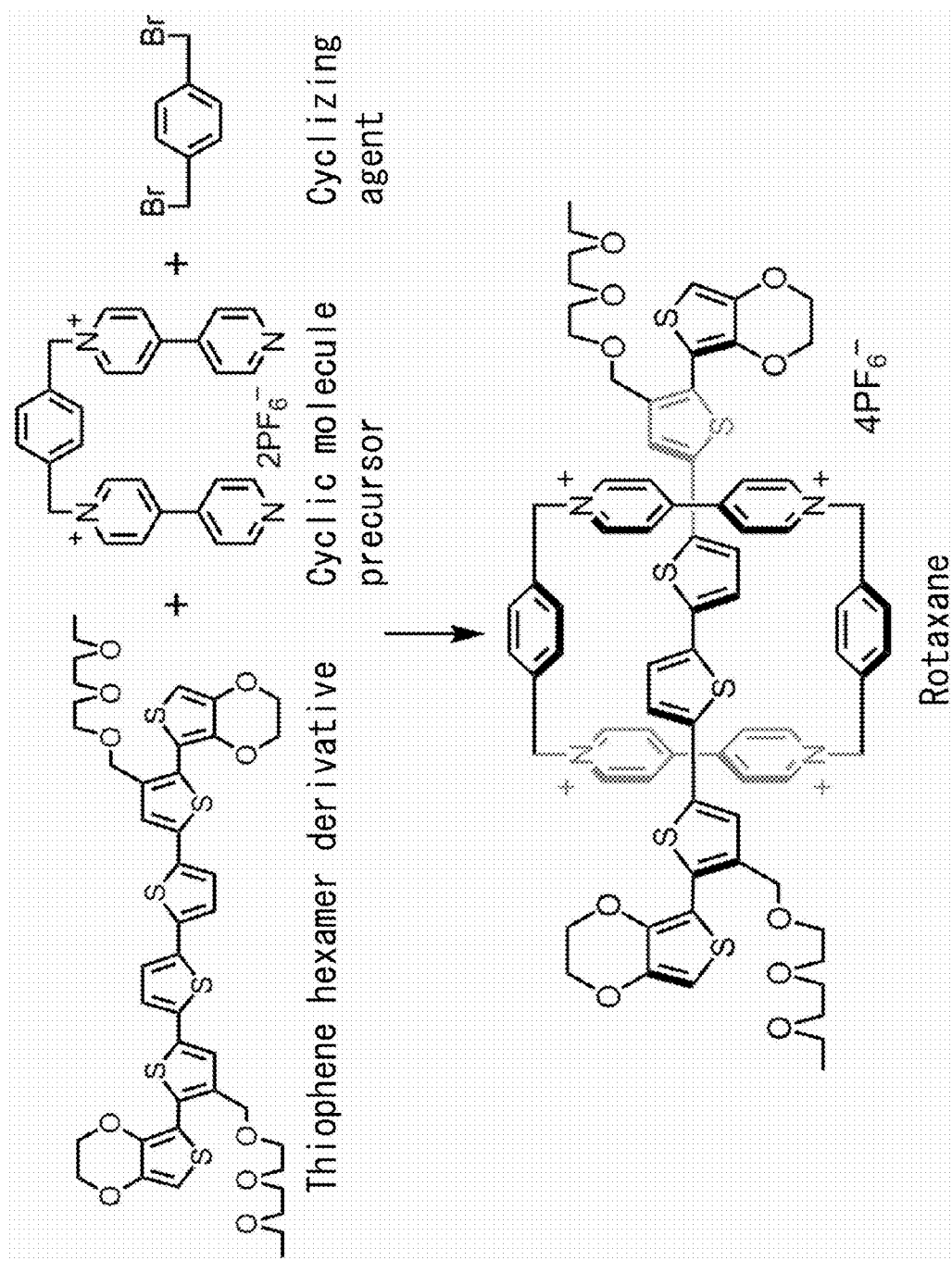
FIG. 2 is a diagram illustrating the synthetic scheme of the example of the present invention.

As shown in FIG. 2 and Table 1, a thiophene hexamer derivative expressed by chemical formula 3, namely 3,4,3'''',4''''-bis(ethylenedioxy)-3',4'''-[2-(2-ethoxyethoxy)ethoxy]methyl-2,2':5',2'':5''',2''':5'''',2''''-sexithiophene, as olygomer, a cyclic molecule precursor (chemical formula 9), and a cyclizing agent α,α'-dibromo-p-xylene (chemical formula 10) were dissolved in acetonitrile or dimethylformamide, and the solution was kept agitated in the argon atmosphere for five to seven days.

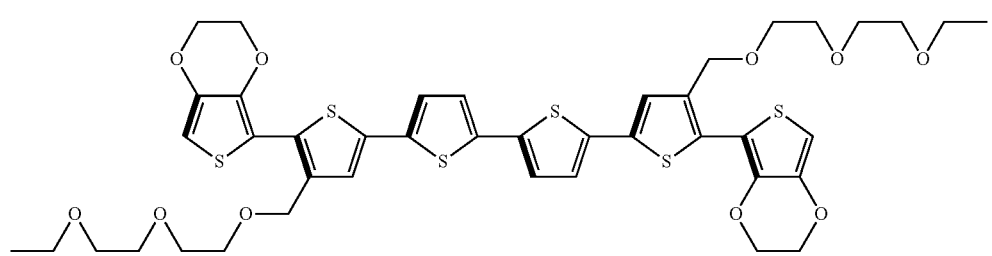

Chemical formula 3

Chemical formula 9

Chemical formula 10

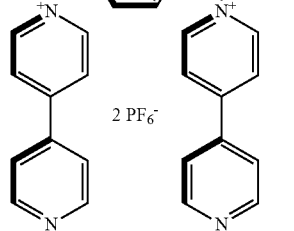

TABLE 1

Rotaxane synthesis conditions and result

| Experiment No. | Starting Material | | Reaction condition | | | | |
|---|---|---|---|---|---|---|---|
| | Thiophene hexamer derivative | Cyclic molecule precursor | Cyclizing agent | Type of solvent | Amount of solvent | Duration | Yield |
| 1 | 90 mg | 140 mg | 50 mg | Acetonitrile | 6 mL | 5 | 10 mol % |
| 2 | 130 mg | 220 mg | 75 mg | Acetonitrile | 5 mL | 6 | 11 mol % |
| 3 | 300 mg | 470 mg | 175 mg | Acetonitrile | 10 mL | 7 | 11 mol % |
| 4 | 270 mg | 1500 mg | 630 mg | Dimethylformamide | 20 mL | 7 | 7 mol % |
| 5 | 300 mg | 470 mg | 175 mg | Dimethylformamide | 10 mL | 7 | 9 mol % |

To decrease the polarity of the solution, 30 mL of acetic ester was added to the reaction solution, the solution was poured directly into a silica gel column to allow the rotaxane to adsorb to silica gel (Silica gel 60N, spherical neutral [KANTO KAGAKU]). To remove unreacted raw materials and byproducts that did not turn into the rotaxane, 100 mL of acetic ether, and then a 9:1 solution of dichloromethane and methanol were kept pouring in until the solution coming out of the silica gel column became completely transparent.

Using a 6:3:1 solution of methanol, 2M ammonium chloride solution and nitromethane, the rotaxane was eluted from the silica gel column. The eluate was condensed using an evaporator, and then to allow the rotaxane to precipitate by counterion exchange, an ammonium hexafluorophosphate solution (11M) was added until precipitate was no longer formed. After the precipitate was recovered by vacuum filtration, vacuum drying was performed to obtain a green solid rotaxane represented by chemical formula 1.

Chemical formula 1

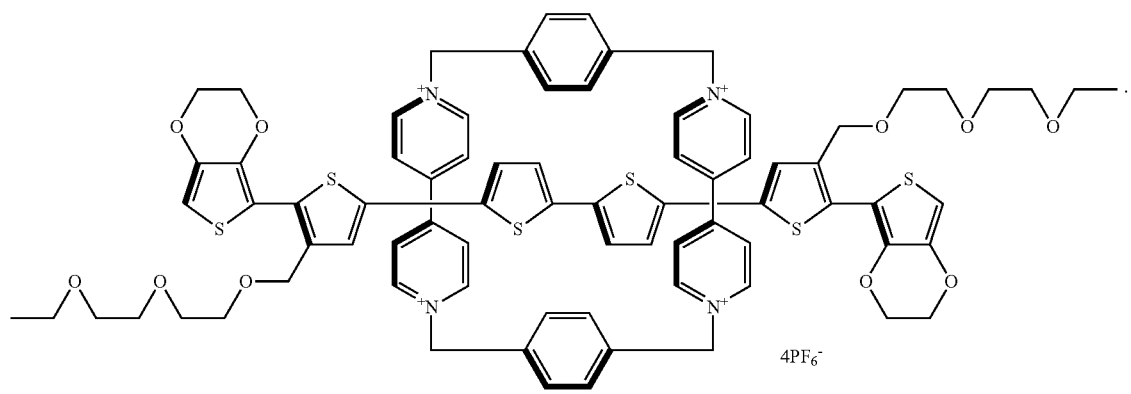

Synthesized rotaxane was confirmed by nuclear magnetic resonance (NMR) and high-resolution mass spectrometry.

The results of NMR and high-resolution mass spectrometry are shown below.

(1) Result of $^1$HNMR (Solvent: CD$_3$CM)

δ=1.01 (6H), 3.41 (4H), 3.58 (4H), 3.67 (4H), 3.76 (4H), 3.79 (4H), 4.38 (8H), 4.48 (4H), 5.57 (2H), 5.78 (8H), 5.89 (2H), 6.69 (2H), 6.78 (2H), 7.79 (8H), 7.88 (8H), 8.95 (8H) ppm.

(2) Result of $^{13}$CNMR (Solvent: CD$_3$CM)

δ=15.4, 65.5, 65.6, 66.3, 66.8, 67.5, 70.3, 71.16, 71.22, 71.4, 101.7, 108.1, 125.5, 126.3, 126.5, 127.6, 131.8, 134.4, 135.0, 136.0, 138.0, 138.2, 140.4, 143.0, 146.0, 148.5 ppm.

Figure 3:
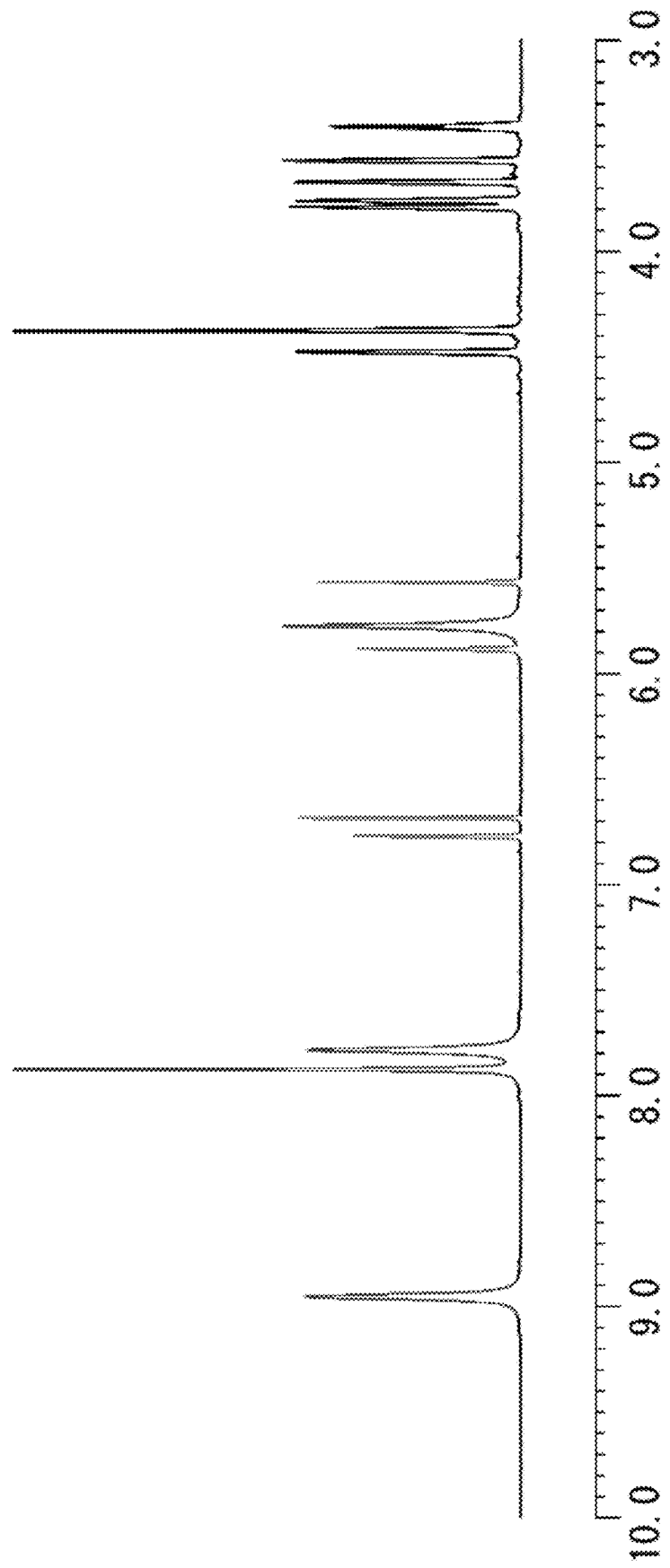
FIG. 3 is a chart illustrating NMR spectrum of the rotaxane of the above example.

FIG. 3 is an NMR chart of the rotaxane obtained in the example.

(3) Result of High-Resolution Mass Spectrometry

Actual measurement value m/z=522.4530 [M+PF$_6$]$^{3+}$

Theoretical value C$_{78}$H$_{78}$F$_6$N$_4$O$_{10}$PS$_6$: m/z=522.4561

<Synthesis of a Polyrotaxane 1>

Figure 4:
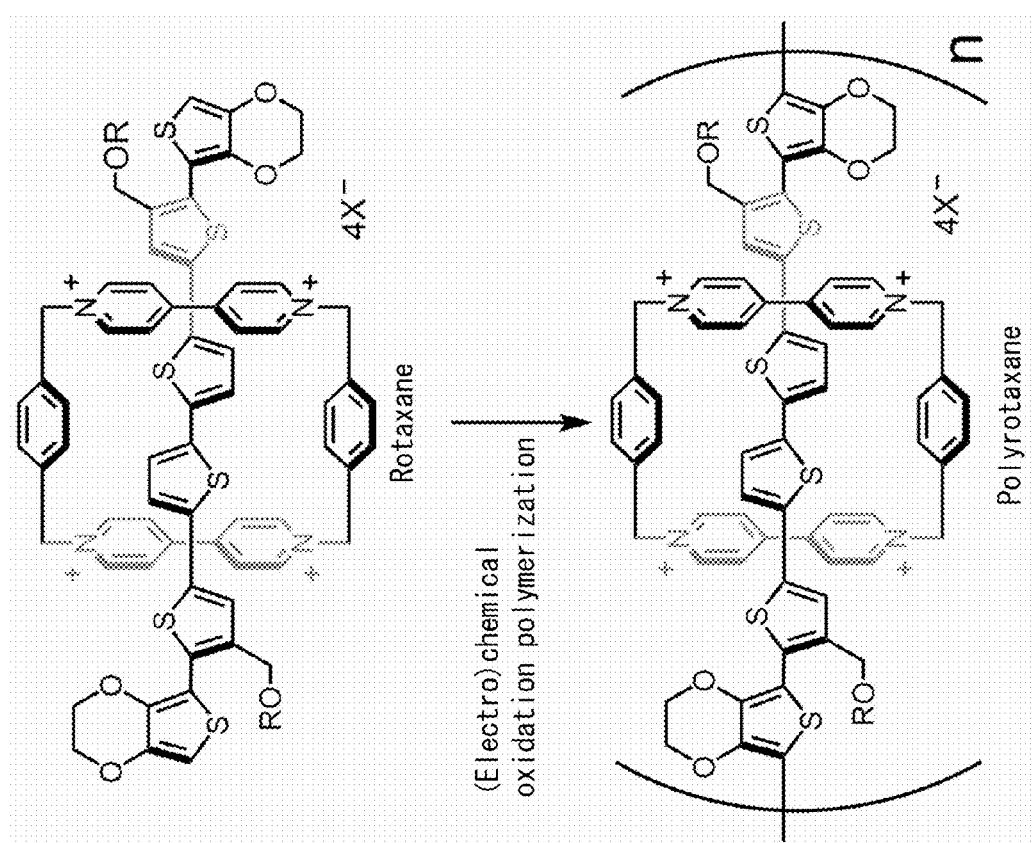
FIG. 4 is a chart illustrating the synthetic scheme of the polyrotaxane of the present invention.

FIG. 4 shows the scheme of synthesizing a polyrotaxane from rotaxanes.

First, by subjecting the rotaxane obtained as described above to electrochemical polymerization, the polyrotaxane was obtained. As shown in Table 2, using an acetonitrile solution containing 0.1 M of tetrabutylammonium perchlorate (TBA.ClO$_4$) or tetrabutylammonium hexafluorophosphate (TBA.PF$_6$), 0.01 to 1 mM of a rotaxane solution was prepared.

As a work electrode, a transparent indium tin oxide (ITO) electrode was used. As counter and reference electrodes, a platinum wire and a saturated calomel electrode (SCE) were used.

TABLE 2

Polyrotaxane film formation conditions and results

| Experiment No. | (1)* Concentration (mM) | (2)* | Voltage range (V) | Work electrode sweep rate | Number of sweep | (3)* | π-π* transition Absorption maximum wavelength | Absorbance |
|---|---|---|---|---|---|---|---|---|
| 1 | 1 | TBA•PF$_6$ | 0.0-1.2 | 100 mV/s | 4 | No | — | — |
| 2 | 1 | TBA•ClO$_4$ | 0.0-1.2 | 200 mV/s | 4 | Yes | 519 nm | 0.42 |
| 3 | 1 | TBA•ClO$_4$ | 0.0-1.2 | 100 mV/s | 4 | Yes | 516 nm | 0.51 |
| 4 | 1 | TBA•ClO$_4$ | 0.0-1.2 | 50 mV/s | 4 | Yes | 516 nm | 0.53 |
| 5 | 1 | TBA•ClO$_4$ | 0.0-1.2 | 100 mV/s | 2 | Yes | 521 nm | 0.34 |
| 6 | 1 | TBA•ClO$_4$ | 0.0-1.0 | 50 mV/s | 4 | Yes | 519 nm | 0.18 |
| 7 | 1 | TBA•ClO$_4$ | 0.0-0.8 | 100 mV/s | 4 | No | — | — |
| 8 | 0.1 | TBA•ClO$_4$ | 0.0-1.2 | 100 mV/s | 4 | Yes | 523 nm | 0.05 |
| 9 | 0.05 | TBA•ClO$_4$ | 0.0-1.2 | 100 mV/s | 4 | Yes | 525 nm | 0.01 |
| 10 | 0.01 | TBA•ClO$_4$ | 0.0-1.2 | 100 mV/s | 4 | No | — | — |

(1)* Rotaxane in experiment No. 2 in Table 1 was used.

(2)* Supporting electrolyte (3)* Formation of film

Figure 5:
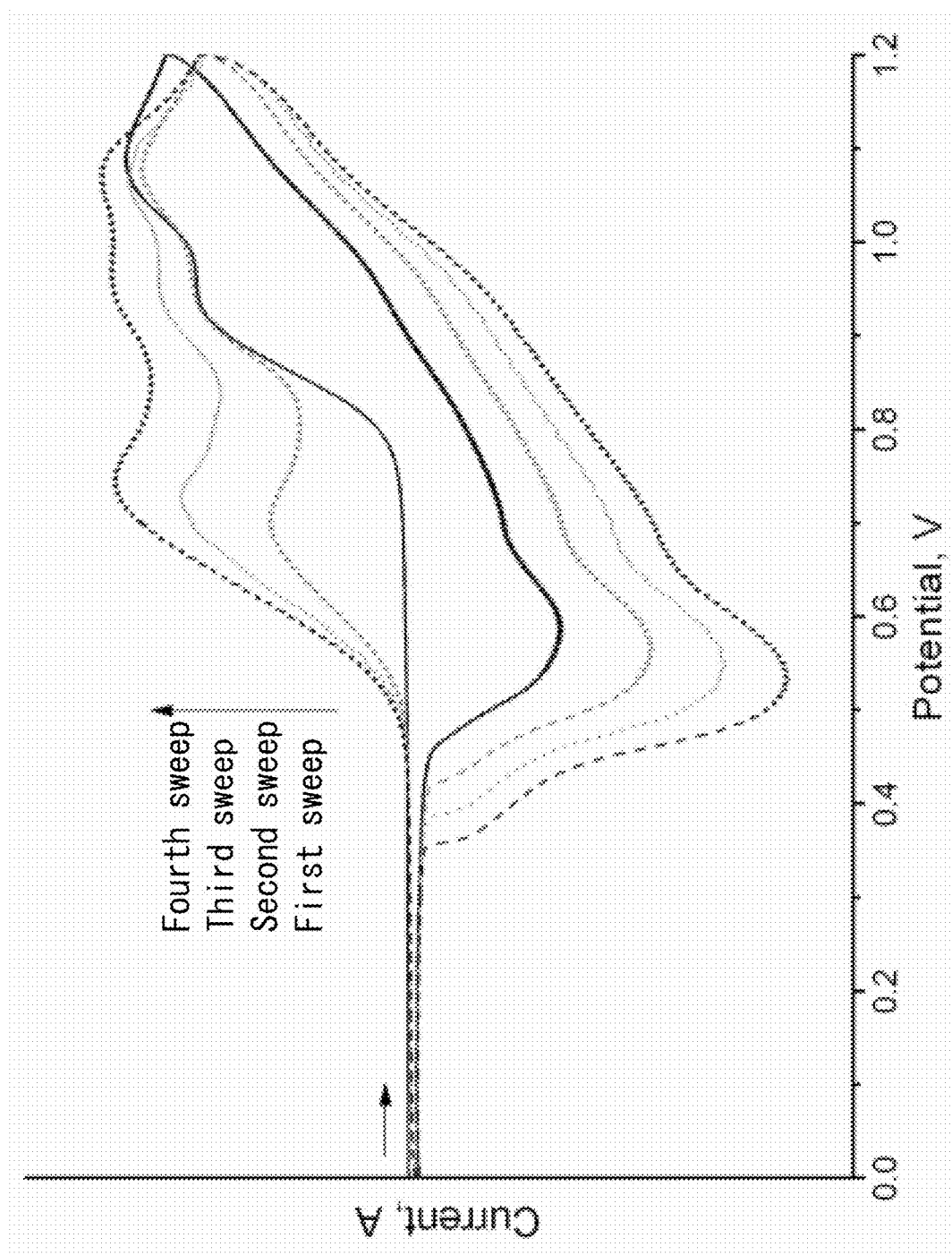
FIG. 5 is a cyclic voltammogram of the rotaxane of the above example.

When the work electrode voltage was changed within the 0 V to 1.2 V range at the sweep rate of 50 mV/s to 200 mV/s, the first peak of oxidation was found when the voltage was 0.8 V or higher, but with the second and subsequent sweep, new oxidation peak was found around 0.6 V. While repeating voltage sweep, the peak was found to fall around 0.6 V (see FIG. 5), which means that electrolytic polymerization occurred on the electrode surface, thus causing thiophene contained in the rotaxane to be polymerized. It is desirable that a supporting electrolyte having low polyrotaxane-soluble property be selected and used.

Figure 6:
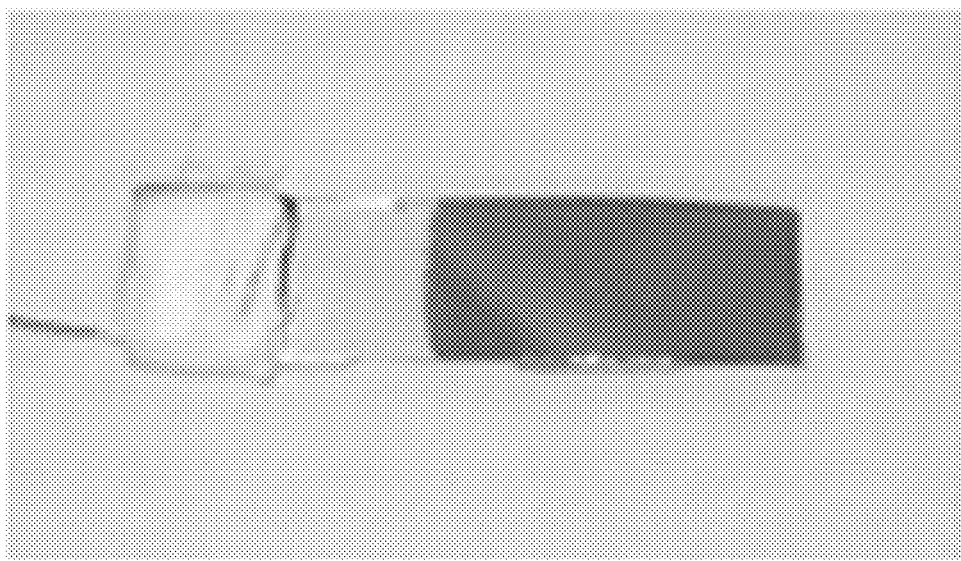
FIG. 6 is a chart showing an image of a polyrotaxane film formed on the indium tin oxide (ITO) electrode of the above example.

As shown in FIG. 6., it was confirmed that a purplish-red film had been formed on the ITO electrode.

The structure of the polyrotaxane obtained in the example is shown by chemical formula 11.

Chemical formula 11

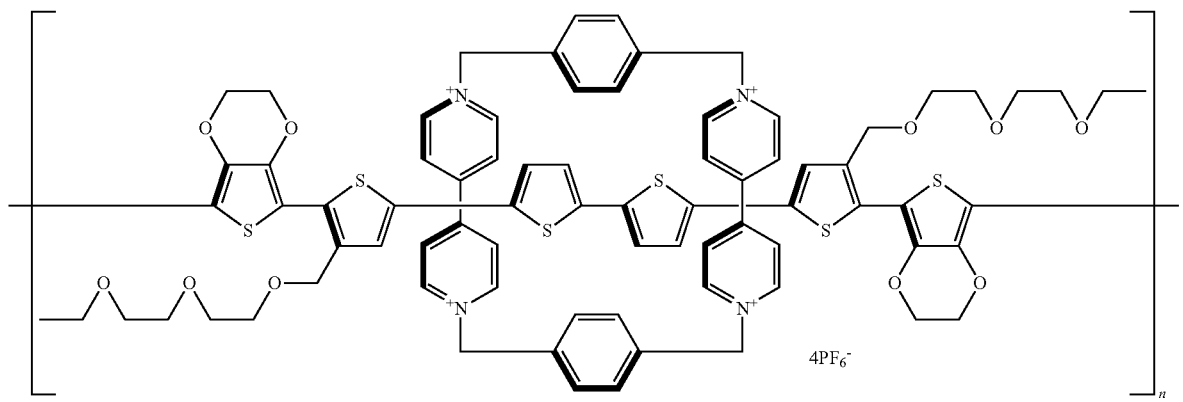

<Synthesis of a Polyrotaxane 2>

Instead of conducting electrochemical polymerization, a polyrotaxane was synthesized by externally adding an oxidizing agent.

10 mg of a rotaxane was dissolved in 0.8 mL of acetonitril, then 7 mg of $Fe(ClO_3)_4$ was added to the solution, and the color of the solution turned from dark purplish red to green, and then to blue. After the solution was agitated for an hour, the reaction solution was dropped into 50 mL of methanol, and then the solution was further agitated for another hour. A centrifugal separator was used to precipitate polyrotaxane, the supernatant liquid was removed by decantation, and then vacuum drying was performed to obtain polyrotaxane powder.

<Optical Characteristics of the Polyrotaxane Film>

Figure 7:
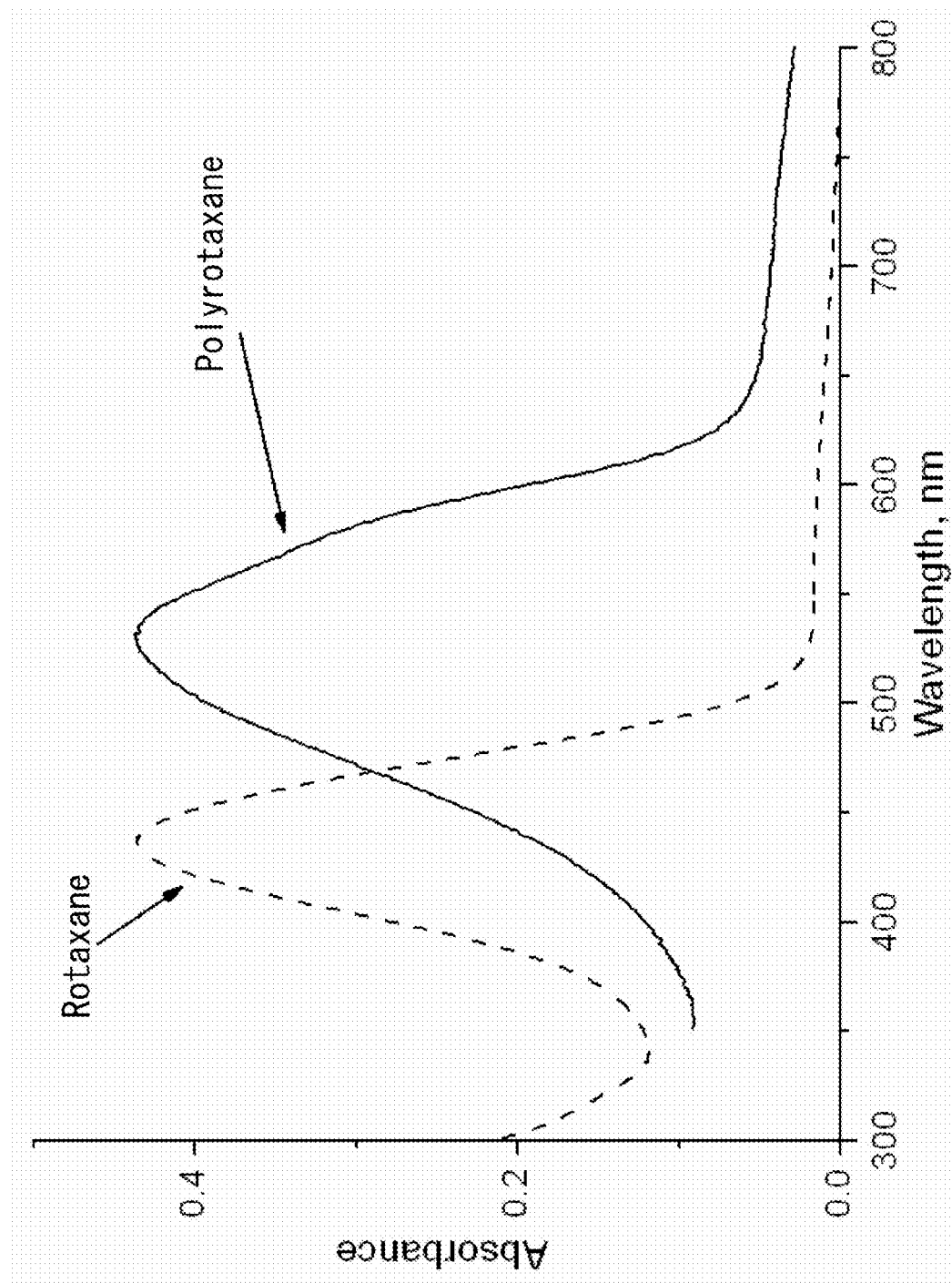
FIG. 7 is a chart illustrating the ultraviolet-visible absorption spectrum of the rotaxane and polyrotaxane film of the above example.

To examine the optical characteristics of the polyrotaxane film formed on the ITO substrate by electrochemical polymerization, the ITO substrate having the polyrotaxane film was placed on an optical path and analyzed using an ultraviolet-visible absorption spectrum analyzer. It was confirmed that as a result of rotaxane turning into polyrotaxane by electrochemical polymerization, the absorption maximum wavelength of π-π*transition shifted from 435 nm to 515-525 nm (see FIG. 7). This shift of absorption maximum wavelength of π-π*transition to longer wavelength represents expansion of π conjugation, meaning that the π-conjugated oligomer has been polymerized into a polymer. The absorption maximum wavelength of π-π*transition of the polythiophene polyrotaxane obtained fell within a small range from 515 to 525 nm irrespective of electrochemical polymerization conditions, which means a film of uniform quality was obtained.

<Electrochemical Measurement of the Polyrotaxane Film>

Figure 8:
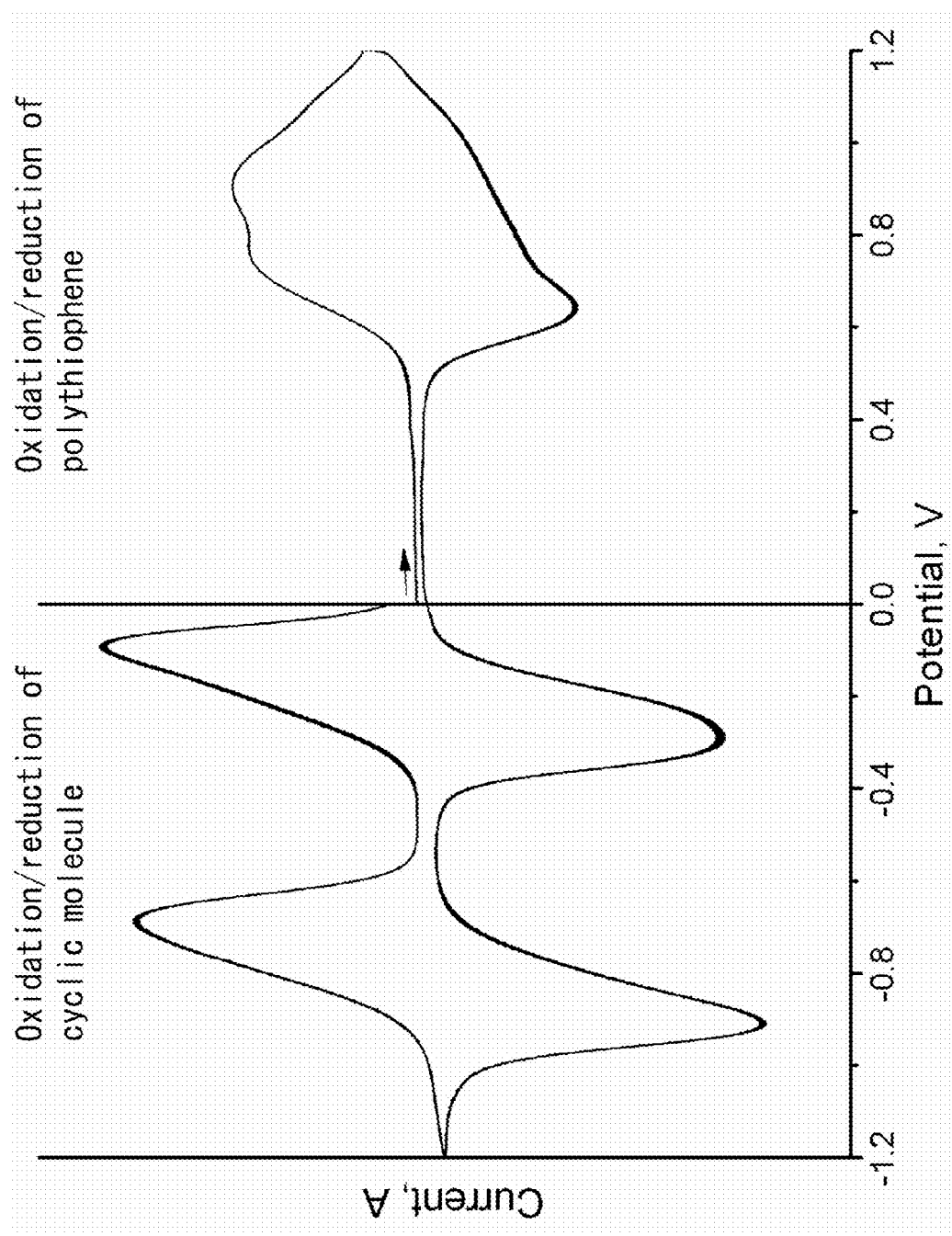
FIG. 8 is a cyclic voltammogram of the polyrotaxane film of the above example.

The electrochemical characteristics of the polyrotaxane film formed on the ITO substrate by electrochemical polymerization were measured by cyclic voltammetry. Polythiophene-derived oxidation/reduction peak was found in the oxidation region (voltage of the work electrode: positive), whereas in the reduction region (voltage of the work electrode: negative), oxidation/reduction peak derived from 4,4'-bipyridinium salt region of the electron-accepting cyclic molecule was found (see FIG. 8). This result confirms that the polytaxane film contains polythiophene and an electron-accepting cyclic molecule.

What is claimed is:

1. A polyrotaxane, comprising rotaxane as a repeating unit having a π-conjugated oligomer and an electron-accepting cyclic molecule,
   wherein each repeating unit having a π-conjugated oligomer contains an electron-accepting cyclic molecule, and
   wherein the polyrotaxane is conductive.

2. The polyrotaxane as set forth in claim 1, wherein the electron-accepting cyclic molecule interacts with a π-conjugated oligomer molecule.

3. The polyrotaxane as set forth in claim 1, wherein the π-conjugated oligomer molecule is at least one selected from the group consisting of the following chemical formulae:

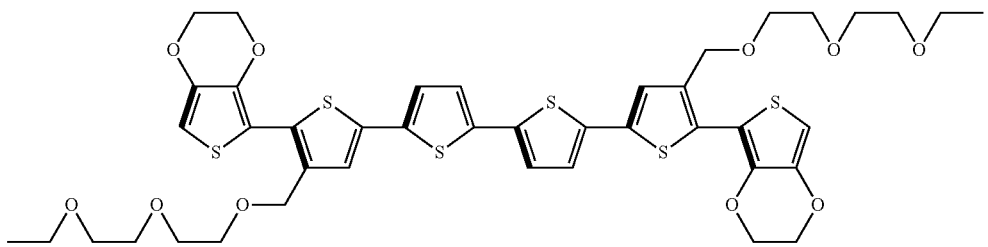 [SMILES: CCOCCOCCOCc1cc(-c2ccc(-c3ccc(-c4cc(COCCOCCOCC)c(-c5scc6c5OCCO6)s4)s3)s2)sc1-c1scc2c1OCCO2]

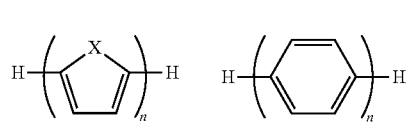
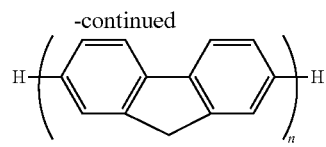
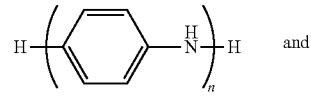
and

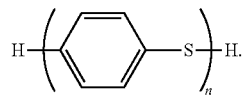

X = NH, O, Se, Te

4. The conductive polyrotaxane as set forth in claim 3, wherein the rotaxane is represented by the following chemical formula:

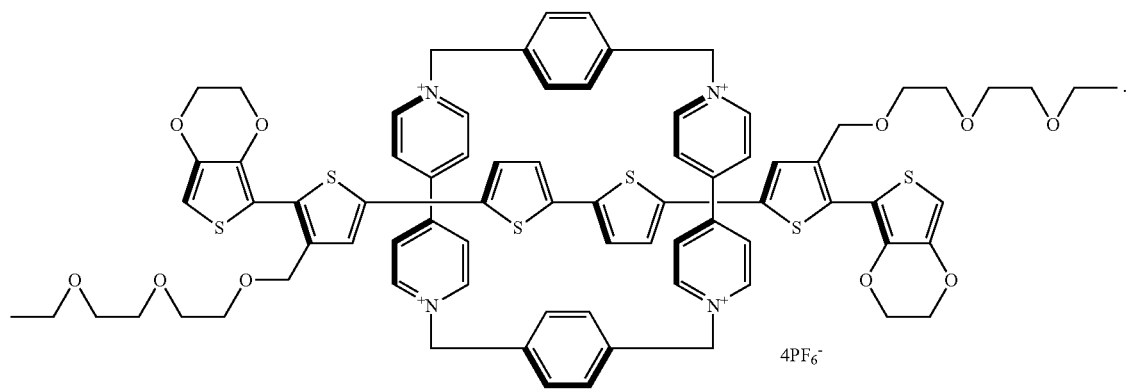

4PF$_6^-$

5. A method of synthesizing a polyrotaxane, comprising: reacting a rotaxane obtained by allowing a π-conjugated oligomer, cyclic molecule precursor, and cyclizing agent in an organic solvent for subjecting oxidation polymerization.

6. The method of synthesizing a polyrotaxane as set forth in claim 4, wherein the π-conjugated oligomer molecule is at least one selected the group consisting of the following chemical formulae:

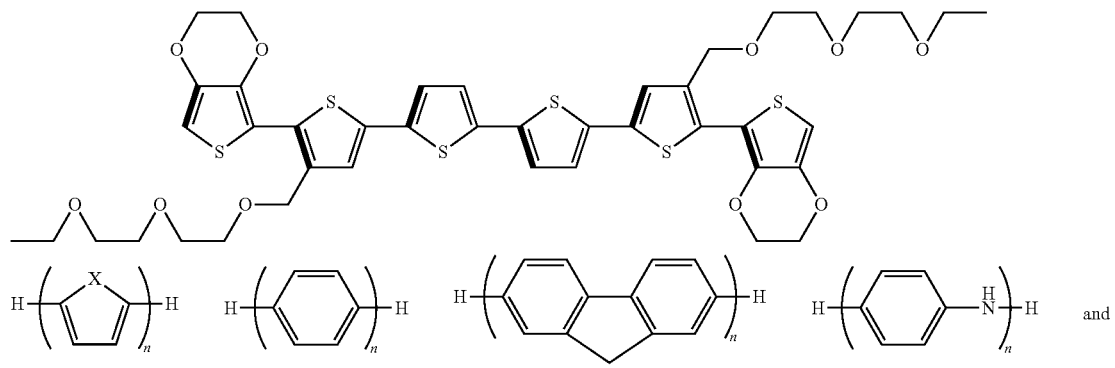

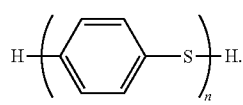

X = NH, O, Se, Te

7. The method of synthesizing a conductive polyrotaxane as set forth in claim 5, wherein the π-conjugated oligomer is expressed by the following chemical formula:
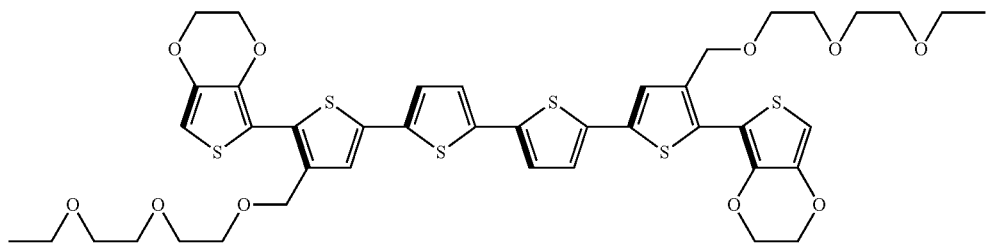
and the cyclic molecule precursor is expressed by the following chemical formula:
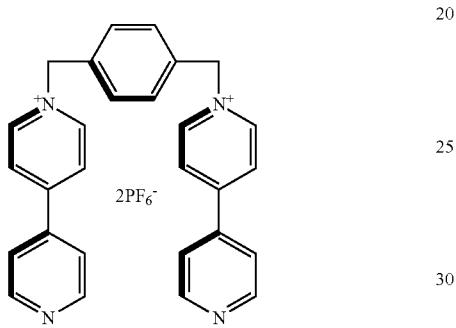
and the cyclizing agent is expressed by the following chemical formula:
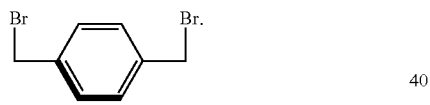
* * * * *

UNITED STATES PATENT AND TRADEMARK OFFICE
CERTIFICATE OF CORRECTION

PATENT NO.       : 8,613,611 B2                                            Page 1 of 1
APPLICATION NO. : 13/264474
DATED            : December 24, 2013
INVENTOR(S)      : Ikeda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 91 days.

Signed and Sealed this
Twenty-second Day of September, 2015

Michelle K. Lee
*Director of the United States Patent and Trademark Office*